United States Patent [19]
Farley et al.

[11] Patent Number: 6,033,398
[45] Date of Patent: *Mar. 7, 2000

[54] METHOD AND APPARATUS FOR TREATING VENOUS INSUFFICIENCY USING DIRECTIONALLY APPLIED ENERGY

[75] Inventors: Brian E. Farley, Los Altos; Michael D. Laufer, Menlo Park; Dawn A. Henderson, Palo Alto; Douglas M. Petty, Pleasanton; Mark P. Parker, San Jose, all of Calif.

[73] Assignee: Vnus Medical Technologies, Inc., Sunnyvale, Calif.

[ * ] Notice: This patent is subject to a terminal disclaimer.

[21] Appl. No.: 08/811,820

[22] Filed: Mar. 4, 1997

Related U.S. Application Data

[63] Continuation-in-part of application No. 08/610,911, Mar. 5, 1996, and a continuation-in-part of application No. 08/717,994, Sep. 26, 1996, and a continuation-in-part of application No. 08/720,209, Sep. 26, 1996.

[51] Int. Cl.[7] .................................................. A61B 17/38
[52] U.S. Cl. ............................... 606/27; 606/32; 604/20; 604/113; 604/500
[58] Field of Search .................................. 606/27, 40, 41, 606/32, 31; 600/373, 372; 604/107, 104, 105, 106, 19–21, 93, 500, 113; 607/1, 2, 96, 101, 103, 122

[56] References Cited

U.S. PATENT DOCUMENTS

| | | | |
|---|---|---|---|
| 373,399 | 11/1887 | Hamilton . | |
| 659,409 | 10/1900 | Mosher . | |
| 833,759 | 10/1906 | Sourwine . | |
| 985,865 | 3/1911 | Turner, Jr. . | |
| 3,230,957 | 1/1966 | Seifert | 128/407 |
| 3,301,258 | 1/1967 | Werner et al. | 128/303.1 |
| 3,557,794 | 1/1971 | Van Patten | 128/345 |
| 3,920,021 | 11/1975 | Hiltebrandt | 128/303.17 |
| 4,016,886 | 4/1977 | Doss et al. | 128/422 |
| 4,043,338 | 8/1977 | Homm et al. | 128/260 |
| 4,119,102 | 10/1978 | LeVeen | 128/413 |
| 4,154,246 | 5/1979 | LeVeen | 128/784 |
| 4,312,364 | 1/1982 | Convert et al. | 128/804 |
| 4,346,715 | 8/1982 | Gammell | 128/422 |
| 4,522,205 | 6/1985 | Taylor et al. | 128/303.17 |
| 4,643,186 | 2/1987 | Rosen et al. | 128/303.1 |

(List continued on next page.)

FOREIGN PATENT DOCUMENTS

| | | |
|---|---|---|
| 0 189 329 | 7/1986 | European Pat. Off. . |
| 0 205 851 | 12/1986 | European Pat. Off. . |
| 0 629 382 A1 | 12/1994 | European Pat. Off. ........ A61B 17/36 |
| 0 738 501 A1 | 10/1996 | European Pat. Off. ........ A61B 17/28 |
| 3516830 | 11/1986 | Germany . |

(List continued on next page.)

OTHER PUBLICATIONS

O'Reilly, Kevin, Endovenous Diathermy Sclerosis as a Unit of the Armamentarium for the Attack on Varicose Veins; The Medical Journal of Australia, Jun. 1, 1974, p. 900.

(List continued on next page.)

Primary Examiner—Corrine McDermott
Assistant Examiner—Cris Rodriguez
Attorney, Agent, or Firm—Fulwider Patton Lee & Utecht

[57] ABSTRACT

A catheter introduces electrodes in a vein for a minimally invasive treatment of venous insufficiency by the application of energy to cause selective heating of the vein. The catheter is positioned within the vein to be treated, and the electrodes on the catheter are moved toward one side of the vein. RF energy is applied in a directional manner from the electrodes at the working end of the catheter to cause localized heating and corresponding shrinkage of the adjacent venous tissue, which may include commissures, leaflets and ostia. Fluoroscopy or ultrasound may be used to detect shrinkage of the vein. After treating one section of the vein, the catheter can be repositioned to place the electrodes to treat different sections of the vein until all desired venous valves are repaired and rendered functionally competent.

33 Claims, 8 Drawing Sheets

U.S. PATENT DOCUMENTS

| | | | |
|---|---|---|---|
| 4,658,836 | 4/1987 | Turner | 128/804 |
| 4,660,571 | 4/1987 | Hess et al. | 128/784 |
| 4,664,120 | 5/1987 | Hess | 128/642 |
| 4,699,147 | 10/1987 | Chilson et al. | 128/642 |
| 4,709,698 | 12/1987 | Johnston et al. | 128/303.12 |
| 4,765,331 | 8/1988 | Petruzzi et al. | 128/303.14 |
| 4,776,349 | 10/1988 | Nashef et al. | 128/786 |
| 4,807,620 | 2/1989 | Strul et al. | 128/303.1 |
| 4,823,812 | 4/1989 | Eshel et al. | 128/804 |
| 4,945,912 | 8/1990 | Langberg | 128/642 |
| 4,966,597 | 10/1990 | Cosman | 606/50 |
| 4,976,711 | 12/1990 | Parins et al. | 606/48 |
| 4,979,948 | 12/1990 | Geddes et al. | 606/33 |
| 5,010,894 | 4/1991 | Edhag | 128/785 |
| 5,035,694 | 7/1991 | Kasprzyk . | |
| 5,057,106 | 10/1991 | Kasevich et al. . | |
| 5,057,107 | 10/1991 | Parins et al. . | |
| 5,078,717 | 1/1992 | Parins et al. . | |
| 5,098,429 | 3/1992 | Sterzer . | |
| 5,098,431 | 3/1992 | Rydell . | |
| 5,117,828 | 6/1992 | Metzger et al. | 128/642 |
| 5,122,137 | 6/1992 | Lennox | 606/40 |
| 5,156,151 | 10/1992 | Imran | 128/642 |
| 5,188,602 | 2/1993 | Nichols | 604/113 |
| 5,190,517 | 3/1993 | Zieve et al. . | |
| 5,215,103 | 6/1993 | Desai | 128/784 |
| 5,255,678 | 10/1993 | Deslauriers et al. | 128/642 |
| 5,263,493 | 11/1993 | Avitall | 607/122 |
| 5,275,610 | 1/1994 | Eberbach | 606/198 |
| 5,281,218 | 1/1994 | Imran . | |
| 5,293,869 | 3/1994 | Edwards et al. | 128/642 |
| 5,314,466 | 5/1994 | Stern et al. . | |
| 5,370,677 | 12/1994 | Rudie et al. . | |
| 5,370,678 | 12/1994 | Edwards et al. . | |
| 5,383,917 | 1/1995 | Desai et al. | 607/702 |
| 5,397,339 | 3/1995 | Desai | 607/116 |
| 5,403,312 | 4/1995 | Yates et al. . | |
| 5,405,322 | 4/1995 | Lennox et al. | 604/53 |
| 5,405,346 | 4/1995 | Grundy et al. . | |
| 5,409,000 | 4/1995 | Imran | 128/642 |
| 5,411,025 | 5/1995 | Webster, Jr. | 128/642 |
| 5,423,815 | 6/1995 | Fugo . | |
| 5,429,130 | 7/1995 | Goldman | 128/642 |
| 5,431,649 | 7/1995 | Mulier et al. . | |
| 5,437,664 | 8/1995 | Cohen et al. | 606/42 |
| 5,447,529 | 9/1995 | Marchlinksi et al. . | |
| 5,449,381 | 9/1995 | Imran | 607/122 |
| 5,454,809 | 10/1995 | Janssen . | |
| 5,458,596 | 10/1995 | Lax et al. | 606/31 |
| 5,462,545 | 10/1995 | Wang et al. . | |
| 5,465,717 | 11/1995 | Imran et al. | 128/642 |
| 5,472,441 | 12/1995 | Edwards et al. | 606/41 |
| 5,505,730 | 4/1996 | Edwards | 606/41 |
| 5,514,130 | 5/1996 | Baker | 606/41 |
| 5,545,161 | 8/1996 | Imran | 606/41 |
| 5,556,396 | 9/1996 | Cohen et al. | 606/42 |
| 5,607,422 | 3/1997 | Smeets et al. | 606/41 |
| 5,626,578 | 5/1997 | Tihon . | |
| 5,709,224 | 1/1998 | Behl et al. | 128/898 |
| 5,810,804 | 9/1998 | Gough et al. | 606/41 |
| 5,817,092 | 10/1998 | Behl | 606/41 |
| 5,827,268 | 10/1998 | Laufer | 606/28 |
| 5,863,290 | 1/1999 | Gough et al. | 606/41 |
| 5,868,740 | 2/1999 | LeVeen et al. | 606/41 |

FOREIGN PATENT DOCUMENTS

| | | | |
|---|---|---|---|
| WO 90/07303 | 7/1990 | WIPO . | |
| WO 92/12681 | 8/1992 | WIPO . | |
| WO 93/21846 | 11/1993 | WIPO | A61B 17/39 |
| WO 94/07446 | 4/1994 | WIPO . | |
| WO 94/21170 | 9/1994 | WIPO | A61B 5/04 |
| WO 95/10236 | 4/1995 | WIPO | A61B 17/39 |
| WO 95/10322 | 4/1995 | WIPO . | |
| WO 95/10978 | 4/1995 | WIPO . | |
| WO 95/31142 | 11/1995 | WIPO | A61B 17/20 |
| WO 96/32885 | 10/1996 | WIPO | A61B 5/04 |
| WO 97/17892 | 5/1997 | WIPO | A61B 5/04 |

OTHER PUBLICATIONS

Watts, G.T., Endovenous Diathermy Destruction of Internal Saphenous, British Medical Journal, Oct. 7, 1972, p. 53.

O'Reilly, Kevin, Endovenous Diathermy Sclerosis of Varicose Veins, The Australian, New Zealand Journal of Surgery, vol. 47, No. 3, Jun. 1977, pp. 393–395.

O'Reilly, Kevin, A Technique of Diathermy Sclerosis of Varicose Veins, The Australian, New Zealand Journal of Surgery, vol. 51, No. 4, Aug. 1981, pp. 379–382.

Cragg et al., Endovascular Diathermic Vessel Occlusion, Diagnostic Radiology, 144:303–308, Jul. 1982.

Ogawa et al., Electrothrombosis as a Treatment of Cirsoid Angioma in the Face and Scalp and Varicosis of the Leg, Technical Notes, No. 3, Oct., pp. 310–311.

Brunelle, et al., A Bipolar Electrode for Vascular Electrocoagulation with Alternating Current, Radiology, Oct. 1980, vol. 137, pp. 239–240.

Aaron, Electrofulguration for Varicose Veins, the Medical Letter on Drugs and Therapeutics, Jul. 12, 1968, vol. 10, No. 14, Issue 248, p. 54.

Gradman, Venoscopic Obliteration of Variceal Tributaries Using Monopolar Electrocautery, Journal of Dermatology Surgery Oncology, 1994, 20, p. 482–485.

Don Crockett, Jr., M.D., et al., Preliminary Experience with an Endovascular Catheter for Electrocoagulation of Peripheral Veins, The Journal of Vascular Technology, Winter 1996, at 19–22.

Samuel R. Money, M.D., Endovascular Electroablation of Peripheral Veins, 22 Annual Symposium, Current Critical Problems, New Horizons and Techniques in Vascular and Endovascular Surgery (Nov. 1995).

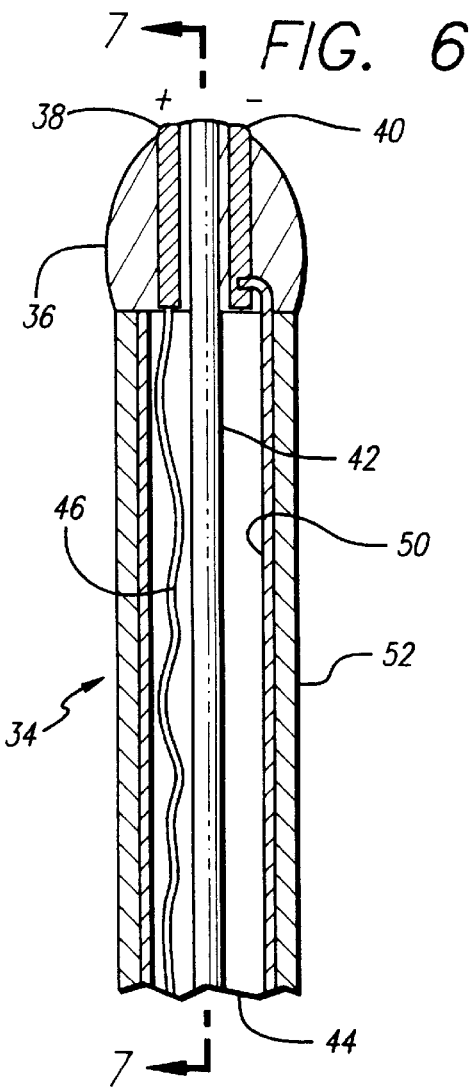
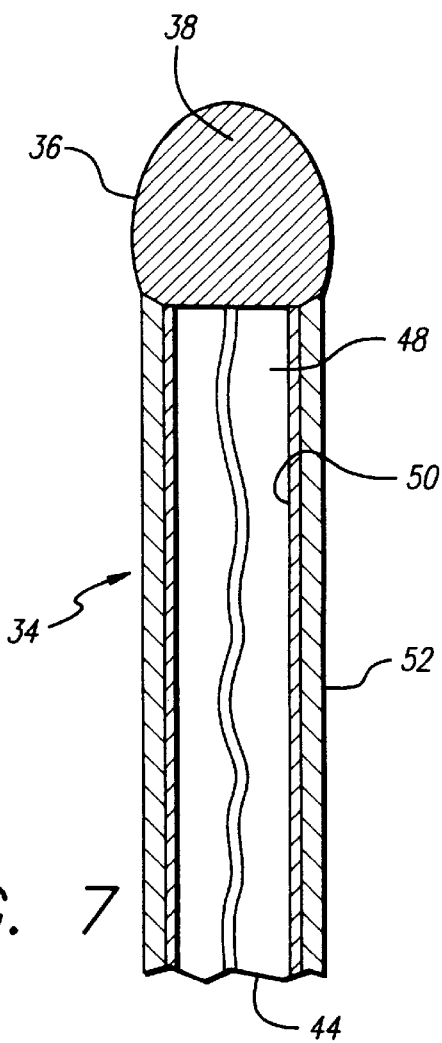
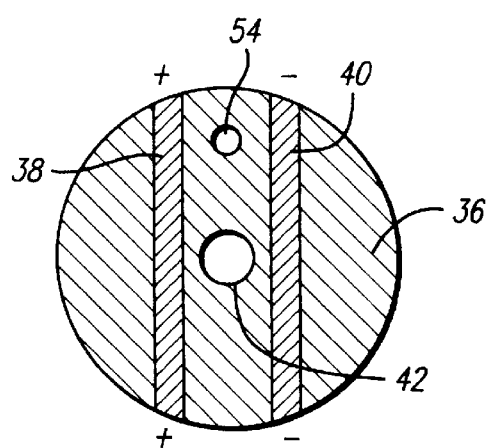
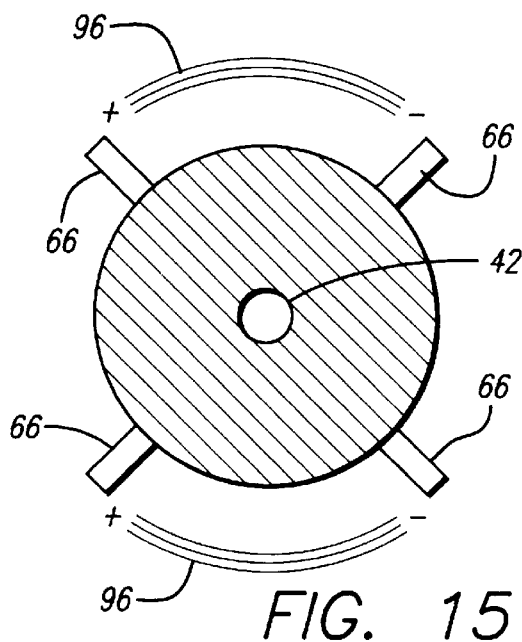

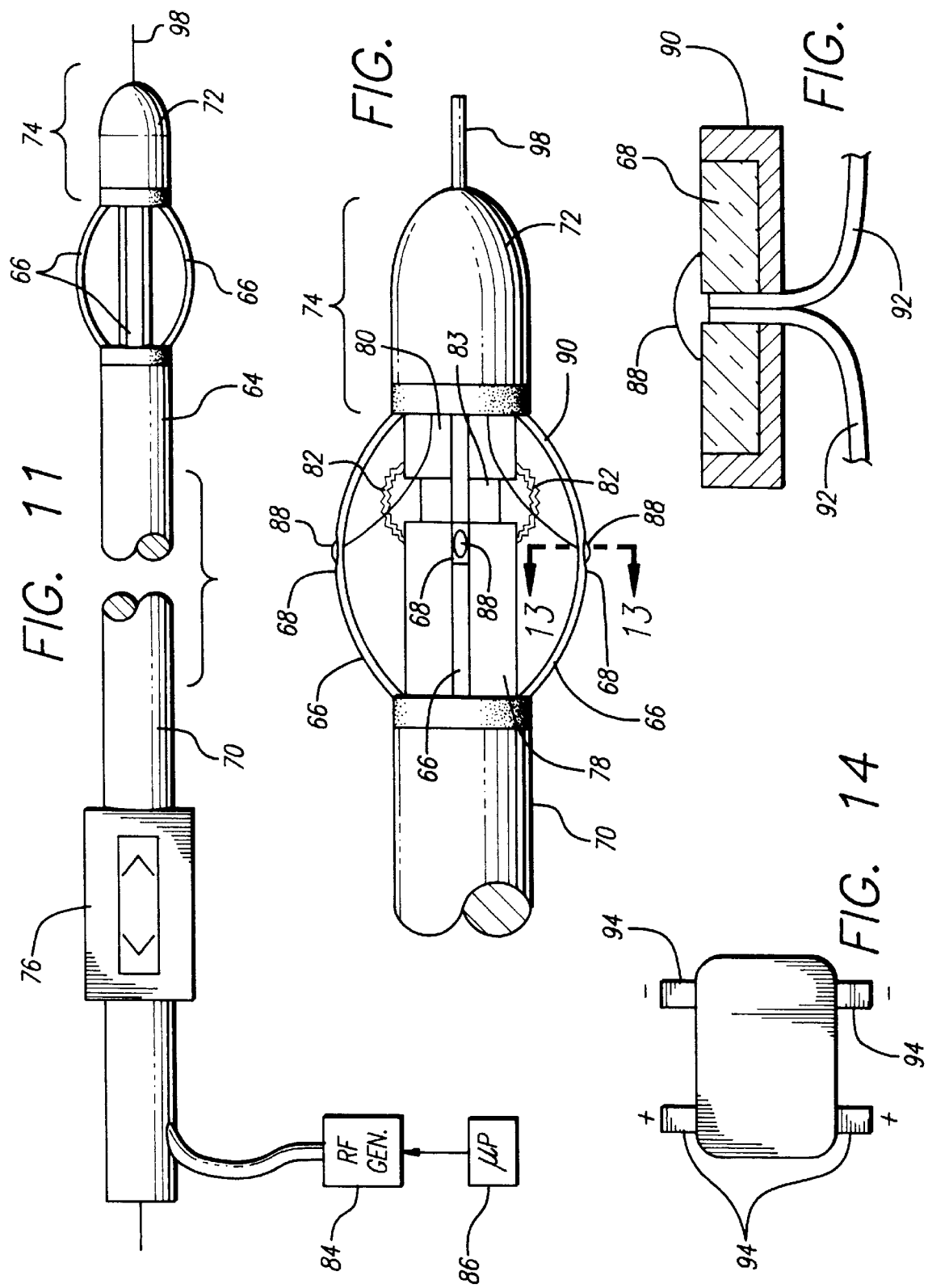

METHOD AND APPARATUS FOR TREATING VENOUS INSUFFICIENCY USING DIRECTIONALLY APPLIED ENERGY

This application is a continuation-in-part of application Ser. No. 08/610,911, filed on Mar. 5, 1996, and Ser. No. 08/717,994 filed on Sep. 26, 1996, and Ser. No. 08/720,209 filed on Sep. 26, 1996.

BACKGROUND OF THE INVENTION

The invention relates generally to the treatment and correction of venous insufficiency, and more particularly, to a minimally invasive procedure and apparatus using a catheter-based system having an energy-delivery arrangement for providing energy intraluminally to shrink a vein to change the fluid flow dynamics, and to restore the competency of venous valves thereby restoring the proper function of the vein.

The human venous system of the lower limbs consists essentially of the superficial venous system and the deep venous system with perforating veins connecting the two systems. The superficial system includes the long or great saphenous vein and the short saphenous vein. The deep venous system includes the anterior and posterior tibial veins which unite to form the popliteal vein, which in turn becomes the femoral vein when joined by the short saphenous vein.

The venous systems contain numerous one-way valves for directing blood flow back to the heart. Venous valves are usually bicuspid valves, with each cusp forming a sack or reservoir for blood which, under retrograde blood pressure, forces the free surfaces of the cusps together to prevent retrograde flow of the blood and allows only antegrade blood flow to the heart. When an incompetent valve is in the flow path, the valve is unable to close because the cusps do not form a proper seal and retrograde flow of blood cannot be stopped.

Incompetence in the venous system can result from vein dilation. Separation of the cusps of the venous valve at the commissure may occur as a result, thereby leading to incompetence. Another cause of valvular incompetence occurs when the leaflets are loose and floppy. Loose leaflets of the venous valve results in redundancy which allows the leaflets to fold on themselves and leave the valve open. The loose leaflets may prolapse, which can allow reflux of blood in the vein. When the venous valve fails, there is an increased strain and pressure on the lower venous sections and overlying tissues, sometimes leading to additional valvular failure. Two venous conditions which often involve vein dilation are varicose veins and more symptomatic chronic venous insufficiency.

The varicose vein condition includes dilatation and tortuosity of the superficial veins of the lower limbs, resulting in unsightly discoloration, pain, swelling, and possibly ulceration. Varicose veins often involve incompetence of one or more venous valves, which allow reflux of blood within the superficial system. This can also worsen deep venous reflux and perforator reflux. Current treatments include surgical procedures such as vein stripping, ligation, and occasionally, vein segment transplant, venous valvuloplasty, and the implantation of various prosthetic devices. The removal of varicose veins from the body can be a tedious, time-consuming procedure having a painful and slow healing process. In addition, patients with varicose veins may undergo injection sclerotherapy, or removal of vein segments. Complications, scarring, and the loss of the vein for future cardiac and other by-pass procedures may also result. Along with the complications and risks of invasive surgery, varicose veins may persist or recur, particularly when the valvular problem is not corrected. Due to the long, technically demanding nature of the surgical valve reconstruction procedure, treating multiple venous sections with surgical venous valve repair is rarely performed. Thus, a complete treatment of all important incompetent valves is impractical.

Non-obstructive chronic venous insufficiency (CVI) is a problem caused by degenerative weakness in the vein valve segment, or by hydrodynamic forces acting on the tissues of the body, especially the legs, ankles and feet. As the valves in the veins fail, the hydrostatic pressure increases on the next venous valves down, causing those veins to dilate. As this continues, more venous valves will eventually fail. As they fail, the effective height of the column of blood above the feet and ankles grows, and the weight and hydrostatic pressure exerted on the tissues of the ankle and foot increases. When the weight of that column reaches a critical point as a result of the valve failures, ulcerations of the ankle begin to form, which start deep and eventually come to the surface. These ulcerations do not heal easily because of poor venous circulation due to valvular incompetence in the deep venous system and other vein systems.

Chronic venous insufficiency often consists of hypertension of the lower limb in the deep, perforating and often superficial veins, and may result in discoloration, pain, swelling and ulceration. Existing treatments for chronic venous insufficiency are often less than ideal. These treatments include the elevation of the legs, compressing the veins externally with elastic support hose, perforator ligation, surgical valve repair, and grafting vein sections with healthy valves from the arm into the leg. These methods have variable effectiveness. Moreover, invasive surgery has its associated complications with risk to life and expense. Similarly, the palliative therapies require major lifestyle changes for the patient. For example, the ulcers may recur unless the patient continues to elevate the legs and use pressure gradient stockings for long continuous periods of time.

Due to the time-consuming and invasive nature of the current surgical treatments, such as valvuloplasty or vein segment grafting, typically only one valve is treated during any single procedure. This greatly limits the ability of the physician to fully treat patients suffering from chronic venous insufficiency. Every instance of invasive surgery, however, has its associated complications with morbidity and expense.

Another type of treatment, the ligation of vascular lumina by cauterization or coagulation using electrical energy from an electrode, has been employed as an alternative to the surgical removal of superficial and perforator veins. However, such ligation procedures also close off the lumen, essentially destroying its functional capability. For example, it is known to introduce an electrode into the leg of a patient, and position the electrode adjacent the exterior of the varicose veins to be treated. Through a small stab incision, a probe is forced through the subcutaneous layer between the fascia and the skin, and then to the various veins to be destroyed. A monopolar electrode at the outer end of the probe is placed adjacent the varicose vein and the return electrode is placed on the skin. Once properly positioned, an alternating current of 500 kiloHertz is applied to destroy the adjacent varicose veins by electrocoagulation. The coagulated veins lose the function of allowing blood to flow through, and are no longer of use. For example, occluding or ligating the saphenous vein would render that vein unavailable for harvesting in other surgical procedures such as coronary by-pass operations.

An approach used to shrink a dilated vein involves the insertion of a catheter that provides RF or other energy to the vein tissue. The amount of energy imparted is controlled so that shrinkage occurs as desired. However, one such device is substantially omni-directional in nature and does not permit the application of energy to only a selected portion of the vein. The directional application of energy from such a catheter to affect only a selected portion of the tissue would be particularly useful in the case where one desires to shrink only the valve commissures and not the remainder of the vein, as an example.

Thus a need exists in the art to treat dilated veins, such as those resulting in varicose veins or from venous insufficiency, to maintain the patency of the veins for venous function, and to restore incompetent valves to valvular competency. Those skilled in the art have recognized a need to be able to provide energy directionally so that only selected portions of tissue are affected. The invention fulfills these needs and others.

SUMMARY OF THE INVENTION

Briefly, and in general terms, the present invention provides a minimally invasive method and apparatus for solving the underlying problems of venous insufficiency and uses a novel repair system, including a directional energy delivery catheter for applying energy to a selected tissue site. A method for venous repair comprises the steps of introducing a catheter having a working end and means for applying energy located at the working end to a treatment site in the vein lumen; positioning the means for heating adjacent the treatment site in the vein lumen; directionally emitting energy from the means for heating to selectively heat the treatment site and cause shrinkage of venous tissue at the treatment site; and terminating the emission of energy from the means for heating after sufficient shrinkage to restore vein competency. An apparatus for applying energy to cause shrinkage of a vein comprises a catheter having a shaft, an outer diameter and a working end, wherein the outer diameter of the catheter is less than the outer diameter of the vein; and an energy delivery apparatus located at the working end to impart energy to the venous tissue. In one aspect, the energy delivery apparatus comprises at least two electrodes located at the working end of the catheter, wherein the electrodes produce an RF field to directionally heat a venous treatment area adjacent the electrode to cause preferential shrinkage of the vein. The energy is applied to a selected circumferential portion of the vein to achieve a reduction of the diameter of the vein.

In another aspect of the invention, an optical energy source may be used to impart directional energy to selectively heat venous tissue.

An aspect of the present invention is to provide an apparatus and method for restoring valvular competence by selectively shrinking the otherwise dilated lumen of the vein by directionally applying energy to tissue.

Another aspect of the present invention is to provide an apparatus and method for controllably shrinking loose, floppy valve leaflets in incompetent valves by directionally applying energy in order to restore valvular competence.

Another aspect of the present invention is to provide an apparatus and method which can treat multiple venous sites in a single procedure.

An additional aspect of the present invention is that no foreign objects or prothesis remain in the vasculature after treatment.

These and other aspects and advantages of the present invention will become apparent from the following more detailed description, when taken in conjunction with the accompanying drawings which illustrate, by way of example, the preferred embodiments of the invention.

BRIEF DESCRIPTION OF THE DRAWINGS

FIG. 6 is a partial cross-sectional plan view of an embodiment of the catheter having an electrode pair and incorporating aspects of the present invention;

FIG. 7 is a cross-sectional view of the embodiment of the catheter incorporating aspects of the invention of FIG. 6 taken along lines 7—7;

FIG. 8 is an end view of the embodiment of the catheter of FIG. 6 in accordance with aspects of the invention;

FIG. 11 is a diagram of a directional RF energy system with a catheter having deployable electrodes for directionally imparting energy to a vein;

FIG. 12 is an enlarged side view of the working end of the embodiment of the directional catheter shown in FIG. 11 showing the bowable electrodes, temperature sensors, guide wire, and stop surface arrangement, in accordance with aspects of the present invention;

FIG. 13 is a partial cross-sectional view of a bowable electrode of the catheter taken across lines 13—13 in FIG. 12 in accordance with aspects of the present invention;

FIG. 14 is a schematic view of mounting deployable discrete electrode pairs so that they remain the same distance apart when they have been expanded;

FIG. 15 is a flux diagram showing the arrangement of discrete electrode pairs to achieve directionality and also shows the primary flux lines resulting from the arrangement;

DETAILED DESCRIPTION OF PREFERRED EMBODIMENTS

Figure 1:
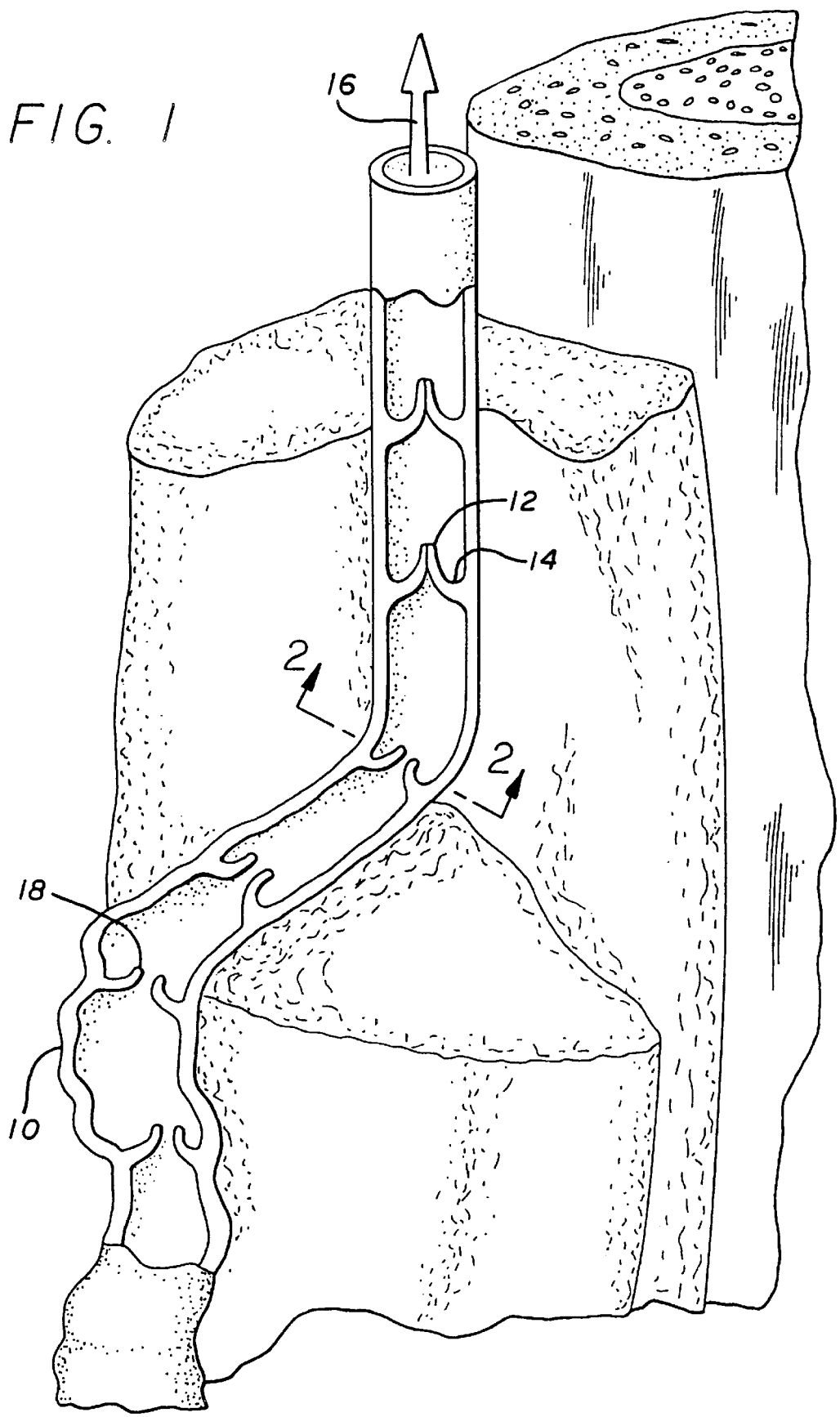
FIG. 1 is a cross-section view of venous insufficiency in a lower limb showing both dilatation of the vein and multiple incompetent valves which is to be treated in accordance with the present invention.

Turning now to the drawings with more particularity, the invention is embodied in a system and method for the intravenous treatment of veins using a catheter to deliver an energy-application element, such as a pair of electrodes, to a venous treatment site. Although described as applying RF energy from the electrode, it is to be understood that other forms of energy such as microwaves, ultrasound, direct current, circulating heated fluid, optical energy, radiant light, and LASERs may be used, and that the thermal energy generated from a resistive coil or curie point element may be used as well. As used herein, like reference numerals will designate corresponding or similar elements in the various embodiments of the present invention to be discussed. In addition, unless otherwise noted, the term "working end" will refer to the direction toward the treatment site in the patient, and the term "connecting" end will refer to the direction away from the treatment site in the patient. The following embodiments are directed to the treatment of the venous system of the lower limbs. It is to be understood, however, that the invention is not limited thereto and can be employed intraluminally to treat veins in other areas of the body such as hemorrhoids, esophageal varices, and venous-drainage-impotence of the penis.

A partial cross-sectional view of a dilated vein 10 from a lower limb having incompetent valves is shown in FIG. 1. These veins are often disposed within muscle tissue. Veins have bicuspid valves, and in a normal and competent valve 12, as shown in the upper part of the vein, each cusp forms a sack or reservoir 14 for blood which, under pressure, forces the free edges of the cusps together to prevent retrograde flow of the blood and allow only antegrade flow to the heart. The arrow 16 leading out the top of the vein represents the antegrade flow of blood back to the heart. The venous valves prevent retrograde flow as blood is pushed forward through the vein lumen and back to the heart.

When an incompetent valve 18, such as those shown in the lower part of the vein, encounters retrograde flow, the valve is unable to close, the cusps do not seal properly, and retrograde flow of blood may occur. Incompetent valves may result from the stretching of dilated veins. As the valves fail, increased pressure is imposed on the lower veins and the lower valves of the vein, which in turn exacerbates the failure of these lower valves. The valve cusps can experience separation at the commissure due to the thinning and stretching of the vein wall at the cusps. Valves can also become incompetent as a result of loose, floppy valve leaflets that can prolapse in response to retrograde blood flow or high proximal venous pressure.

Figure 2:
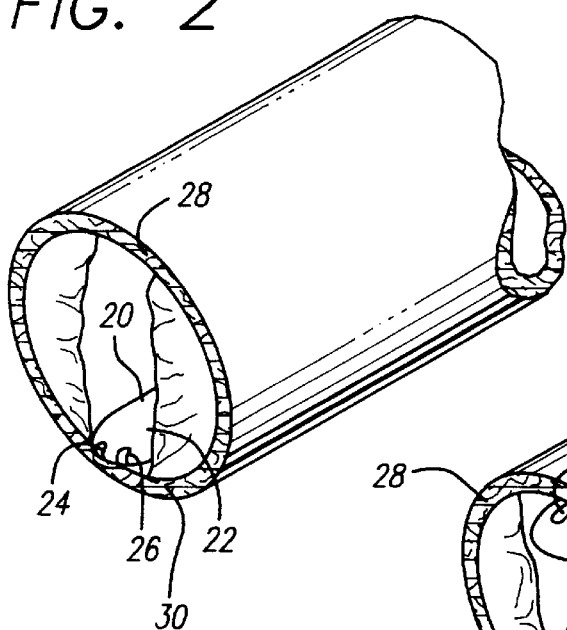
FIG. 2 is a representative view of a venous section having an incompetent valve taken along lines 2—2 of FIG. 1 which is being treated at one commissure by a catheter having an electrode pair, in accordance with aspects of the present invention.

A method of minimally invasive treatment of venous insufficiency and valvular incompetency includes utilizing a catheter to deliver bipolar electrodes to a venous treatment site. A cross-sectional perspective view of a dilated vein taken along lines 2—2 of FIG. 1 is illustrated in FIG. 2. The electrodes directionally provide RF energy at the working end of the catheter to heat and shrink selected venous tissue between the electrodes. The directional application of RF energy in effect forms a heating zone along a portion of the catheter, and allows for localized or preferential heating of venous tissue so that shrinkage of the venous tissue can be limited to selected areas of the vein, such as the commissures of venous valves to restore venous valvular competency. For example, the venous tissue at the commissures can be heated, and the resulting shrinkage can bring the cusps of the venous valve closer together to restore competency. Further shrinkage of the cusps and leaflets can be achieved, if necessary, by moving or rotating the catheter and applying RF energy directionally to the leaflets to cause localized preferential heating and shrinking of the valve leaflets. The outcome of this directional application of RF energy is similar in effect to surgically placing reefing sutures into a floppy valve leaflet during venous valvuloplasty surgery.

Selectively heating a circumferential portion of the vein results in controlled shrinkage of the vein while avoiding the application of energy to the entire vein wall. By the method and apparatus disclosed, the entire vein wall need not be subjected to heating energy, yet shrinkage of the vein diameter can be effected.

An embodiment of the catheter 20 having a working end 22 having a pair of electrodes for 24 and 26 causing localized heating of the surrounding venous tissue and shrinkage of the vein is illustrated in FIGS. 2 through 6. This and other embodiments of the catheter 20 will be described in greater detail later. The working end 22 includes electrodes 24 and 26 for providing RF energy to form a localized heating zone in the tissue at and between the electrodes. The electrodes 24 and 26 can be conductive strips, plates, or wires embedded in the working end 22 of the catheter. RF energy conducted between the electrodes 24 and 26 through contacting venous tissue causes that tissue and surrounding adjacent venous tissue to be heated and shrink. The RF energy is directional between the electrodes of the catheter, and can be directionally applied to the surrounding venous tissue, including the commissures, cusp and leaflets of the venous valves, or to a specific radial arc of the vein wall.

The method of the present invention for the minimally invasive treatment of venous insufficiency preferably uses RF electrodes and a delivery catheter to restore the competency of a vein. Alternatively, the method is contemplated to be used with any suitable appliance for directionally applying radiant energy or heat in the repair or reconfiguration of incompetent veins. The electrodes for generating the heating effect for shrinking the surrounding venous tissue can be introduced either antegrade or retrograde. Particular discussion will be made of the treatment of varicose veins in the legs, though the method is well suited to treating veins in other areas of the body.

When treating the veins of the lower limbs, the patient is typically placed onto a procedure table with the feet dependent in order to fill the veins of the leg. The leg of the patient is prepped with antiseptic solution. A percutaneous introducer is inserted into the vein using a common Seldinger technique to access the saphenous or deep vein system. Alternatively, a venous cut-down can be used to access the vein system to be treated. The procedure for the repair of incompetent veins can be accomplished by a qualified physician with or without fluoroscopic or ultrasonic observation, or under direct visualization. Further, the physician could palpate the treatment area to determine the location of the catheter, and the treatment site, during the procedure when treating the superficial venous system. The physician may also palpate the vein into apposition with the electrodes to achieve good contact between the electrodes and the vein wall.

The delivery catheter 20 could be passed within the vein after insertion through the skin. Alternatively, a guide wire for the catheter can be inserted into the vein. The wire is advanced antegrade to the level of the most proximal incompetent vein valve which is to be repaired. The delivery catheter is then inserted upon the wire and is fed up the leg through the vein to the level of the dilated venous section to be treated. Fluoroscopy, ultrasound, or an angioscopic imaging technique is then used to direct the specific placement of the catheter and confirm the position within the vein. Contrast material can be injected through or around the catheter to identify the incompetent venous sections to be repaired. A retrograde venogram can be performed in some cases to better localize the treatment site and effect.

From the antegrade approach, the catheter can be placed adjacent the incompetent valve of the vein to be treated. As shown in FIG. 2, the catheter 20 travels to a venous valve, and is positioned so that the electrodes can treat specific portions of the vein. The catheter 20 can be manipulated or torqued so that the working end 22 of the catheter is positioned to one side of the valve along the commissure. Alternatively, the catheter can include cables, an inflating balloon, or bowable members which can selectively move the catheter to one side in order to properly position the working end of the catheter against selected venous tissue.

When the electrodes 24 and 26 of the catheter 20 are positioned at the treatment site of the incompetent venous section, an RF generator, electrically connected to the electrodes, is activated to provide suitable RF energy, preferably at a selected frequency from a range of 250 kHz to 350 mHz. One suitable frequency is 510 kHz. One criterion used in selecting the frequency of the energy to be applied is the control desired over the spread, including the depth, of the thermal effect in the venous tissue. Another criterion is compatibility with filter circuits for eliminating RF noise from thermocouple signals.

The RF energy is converted within the adjacent venous tissue into heat, and this thermal effect causes the venous tissue to shrink. The shrinkage is due to structural transfiguration of the collagen fibers in the vein. The collagen fibrils shorten and thicken in cross-section in response to the heat from the thermal effect. Although the collagen becomes more compacted during this process, it still retains some elasticity. When RF energy is applied to the venous tissue at and around the incompetent valve of the dilated vein, the shrinkage of the venous tissue at the commissures can restore valvular competency by reducing the dilation which is preventing the proper functioning of the venous valve. RF energy is directionally applied to treat one commissure 28, as shown in FIG. 2. The catheter is then moved to treat the commissure 30 on the opposite side of the vein, as shown in FIG. 3.

Figure 4:
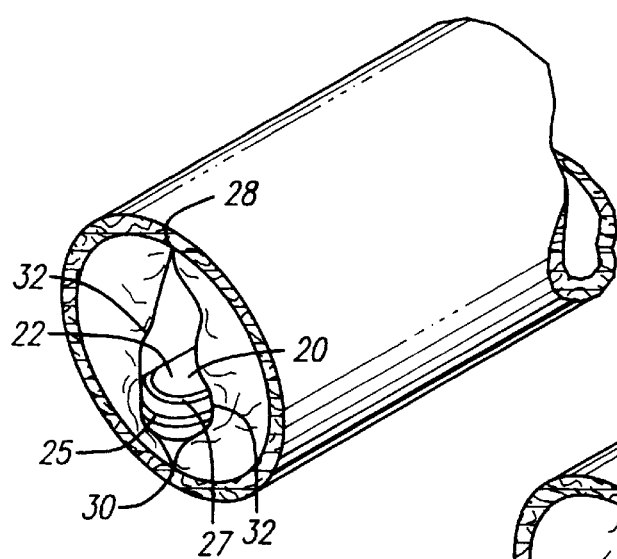
FIG. 4 is a cross-sectional view of treatment of the leaflets of the valve of FIGS. 2 and 3 in accordance with aspects of the present invention.

Gross shrinkage of the vein diameter or shrinkage of the venous tissue at the commissures 28 and 30 can restore competency to the venous valve, where the valve leaflets 32 are brought closer together. If the valve should remain incompetent, and continue to close improperly with prolapsing leaflets 32, manipulating and rotating the working end 22 of the catheter 20 for the further application of RF energy to the leaflets 32 of the venous valve, as shown in FIG. 4, can shrink the otherwise stretched and prolapsing leaflets 32 of the incompetent valve to restore valve competency if necessary. Where the leaflets 32 remain apart, energy applied directly to the leaflets of near the leaflets may cause them to move closer together. An approach is shown in FIG. 4 where energy is applied to the edges of the leaflets to cause them to move closer together. Applying energy to the edges of the leaflets is preferred over applying energy directly to the centers of the leaflets. However, energy can also be applied to the centers.

Figure 5:
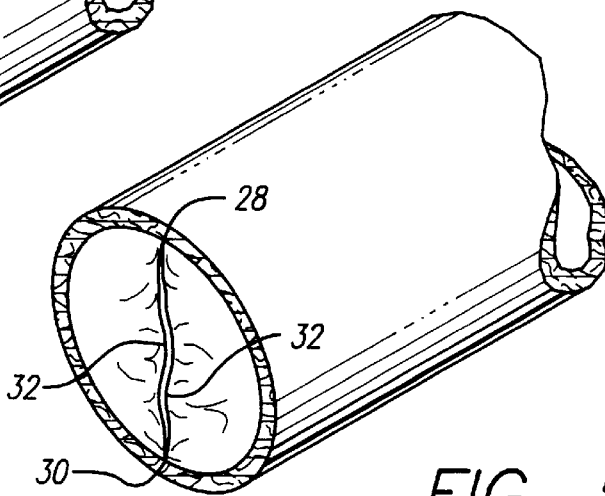
FIG. 5 is a cross-sectional view of the valve of FIGS. 2, 3 and 4 after successful treatment showing that it is once again competent.

Preferentially shrinking the venous tissue in and around the venous valve is shown in the front diagrammatic, cross-sectional views of FIGS. 2 through 5. Competency, as shown in FIG. 5, of the valve is restored by this process. A deflection means such as a bowable member or balloon or other means may be mounted on one side of the distal end of the catheter and deployed to selectively position the catheter at the site. Alternatively, other means may be used to selectively position the catheter distal end, such as a steering cable or cables.

Figure 3:
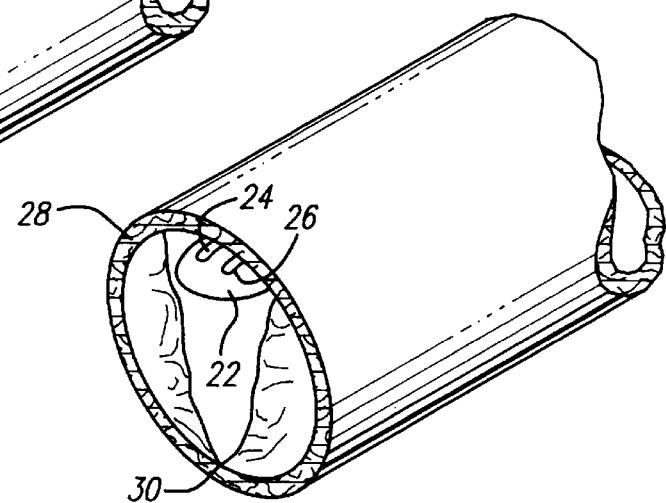
FIG. 3 is a representative view of the venous section shown in FIG. 2 which is being treated at the opposite commissure by the same electrode-pair catheter, in accordance with aspects of the present invention.
Figure 19:
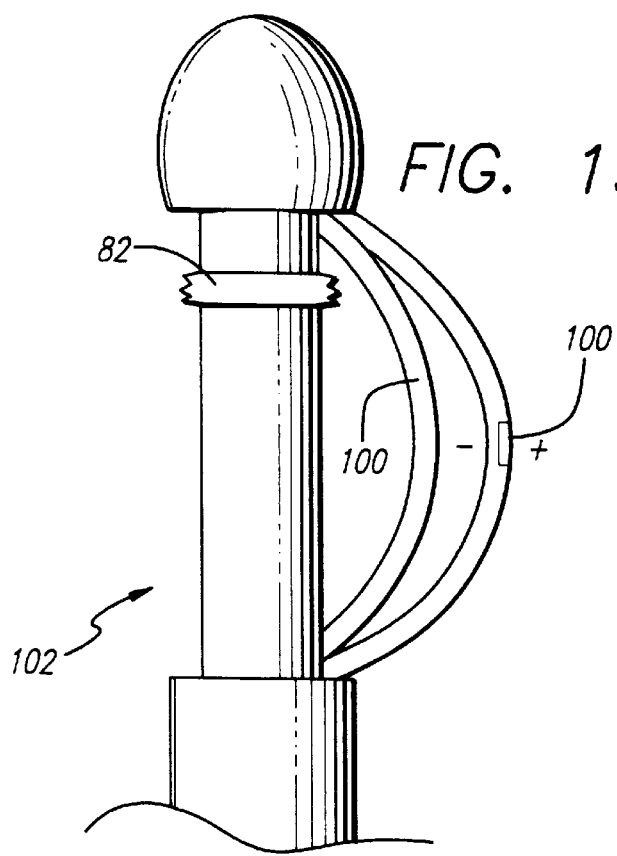
FIG. 19 is a side view of another embodiment of a catheter having one pair of bowable electrodes in accordance with aspects of the present invention.
Figure 20:
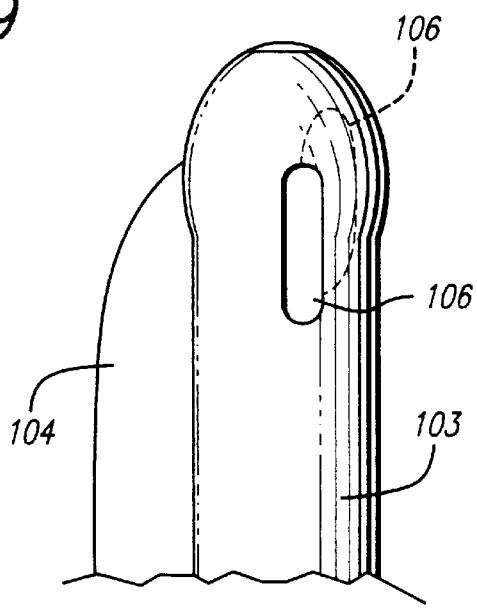
FIG. 20 is a side view of another embodiment of a catheter having a balloon formed on the catheter shaft opposite one pair of electrodes in accordance with aspects of the present invention.

In FIGS. 2 and 3, a catheter 20 having electrodes 24 and 26 only on one side is shown. This is the preferred arrangement so that the possibility of heating the blood is reduced. Such a catheter, and a positioning device, is shown in FIGS. 19 and 20, discussed later. The catheter 20 shown in FIG. 4 on the other hand has electrodes 25 and 27 that extend over opposite sides of the catheter shaft at the working end 22. This has the advantage of allowing the application of energy to both leaflet edges simultaneously.

Vein dilation is reduced after RF energy applied from the electrodes heats the surrounding venous tissue to cause shrinkage. RF energy is no longer applied after there has been sufficient shrinkage of the vein to alleviate the dilation of the vein near the valves, so as to restore venous function or valvular competency. Sufficient shrinkage can be detected by fluoroscopy, external ultrasound scanning, intravascular ultrasound scanning, direct visualization using an angioscope, or any other suitable method. For example, the catheter 20 can be configured to deliver an x-ray contrast medium to allow visualization by fluoroscopy for assessing the condition of the vein and the relationship of the catheter to the treatment area of the vein during the shrinkage process. As an alternative to fluoroscopy, external ultrasound techniques such as B-scanning using distinct ultrasound signals from different angles, or intravascular ultrasound can be used to acquire a more multidimensional view of the vein shrinkage at the treatment site. An angioscope can also be used to directly visualize and determine the extent and degree of vein shrinkage.

After treatment, the commissures and the cusps of the venous valves should be closer together with little separation or prolapse, and a restoration of the competency of the valve is achieved. Valvular competence can be determined by contrast injection or Doppler probe measurement.

Substantial shrinkage may occur very rapidly, depending upon the specific treatment conditions. Because the shrinkage can proceed at a rather rapid rate, the RF energy is preferably applied at low power levels. The properties of the treatment site, such as temperature, can be monitored to provide feedback control for the RF energy in order to minimize coagulation. Other techniques such as impedance monitoring, and ultrasonic pulse echoing, can be utilized in an automated system which shuts down the application of RF energy from the electrodes to the venous section when sufficient shrinkage of the vein is detected and to avoid overheating or coagulation in the vein. Monitoring these values in an automatic feedback control system for the RF energy can also be used to control the spread, including the depth, of the heating effect. In all instances, the application of RF energy is controlled so as to shrink the venous tissue sufficiently to restore the competency of the venous valve.

After treating the first venous section shown, the catheter 20 is moved to the next venous valve suffering from insufficiency. The catheter 20 can be repositioned to treat as many venous sections and valves as necessary. RF energy is applied to each venous section to be repaired, until all of the desired venous sections are repaired and the valves are rendered competent. Multiple incompetent valves and dilated venous sections can be treated and repaired in a single minimally invasive procedure. If desired, a second introducer can be inserted into the limb of a patient in order to access either the deep or the superficial vein system, whichever has yet to be treated. The catheter can then be used to treat incompetent venous sections in the other vein system.

Where the catheter includes a fluid delivery lumen, such as a guide wire lumen through which cooling fluid may be introduced, the cooling fluid can be delivered to the bloodstream during RF heating of the vein being treated. The delivered cooling fluid reduces any heating effect on the blood, and reduces the risk of heating the blood to the point of coagulation. The fluid may also be delivered through ports formed along the side of the catheter near the working end and the electrodes (not shown).

After completing the RF procedure for each selected venous section, the catheter and electrodes are removed from the vasculature. The access point of the vein would be sutured closed if a cutdown had been performed, or local pressure would be applied after percutaneous sheath removal until bleeding was controlled. A bandage would then be applied. A pressure dressing may be necessary. Elastic pressure gradient stockings may be worn subsequently.

As an alternative to the antegrade approach, the catheter can deliver the electrodes to the venous treatment site from a retrograde approach. The catheter is introduced into a percutaneous sheath that has been inserted through the skin and into the vein in a retrograde direction. The electrodes at the working end of the catheter are advanced until contact with the cusp of the venous valve is observed by fluoroscopy, ultrasound, or other detection method. The catheter is then pulled back slightly to allow treatment of the dilated valve sinus or leaflets in the vein. The catheter is capable of being deflected, torqued, or otherwise moved to allow for proper placement of the electrodes. Manipulating the working end of the catheter enables preferential heating along the vein being treated, where the electrodes are placed closer to one side of the vein wall, such as the commissure. The electrodes are activated to deliver RF energy to the venous tissue and shrink the vein. Placing the electrodes in close apposition to the commissures of the venous valve to cause local or preferential shrinkage near the commissures can remedy separation of the commissures from vein dilation and restore venous function and valvular competency. After treating one end of the valvular commissure, the catheter can then be torqued to place the electrodes near the commissure at the opposite end of the valve. After the venous tissue at the commissures are shrunk, and the procedure can be repeated for the valve leaflets if necessary.

A partial cross-sectional plan view of an embodiment of a catheter 34 is shown in FIG. 6. The tip of the working end 36 of the catheter can be formed from polymers or other non-conductive materials. Both electrodes 38 and 40 are preferably made from stainless steel. In one embodiment, the electrodes may take the form of electrode plates as shown in FIG. 7, which is a cross-sectional view taken along lines 7—7 of FIG. 6. The electrodes can be flush with or protrude slightly from the surface of the non-conductive working end of the catheter. Further, the electrodes can be slightly recessed at the front tip of the working end so as to minimize the formation of an RF field in front of the catheter.

Figure 10:
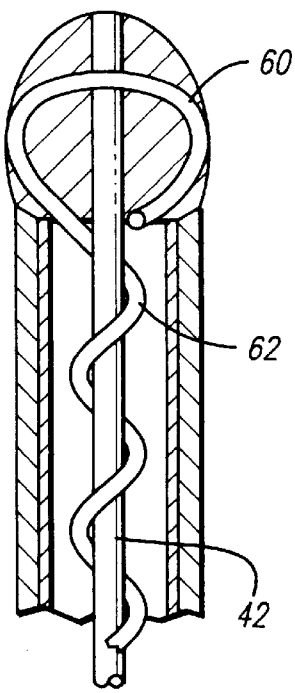
FIG. 10 is yet another view of another embodiment of a catheter having two electrodes in accordance with aspects of the present invention.

In another embodiment, the electrodes can be wires located along or embedded in the surface of the working end 36 as shown in FIG. 10. In this embodiment, the wires generate heat when suitable energy is applied. For example, the wires may be formed of a resistive material and heat up when electricity is conducted through them.

An end view of the working end of the bipolar electrode catheter 34 is shown in FIG. 8. The electrodes are connected to an RF generator so that they have opposite polarity. Therefore, current will flow between them through contacting venous tissue. This arrangement results in a directional application of energy localizing the energy along a portion of the catheter at the working end. The port 42 at the working end can provide cooling fluid or contrast injections to the vein during treatment.

The working end 36 of the catheter 34 is rounded to provide an atraumatic tip for the catheter as it is manipulated within the vein lumen. The outer diameter (O.D.) of the working end, in this case, is slightly larger than the dimensions of the catheter shaft 44. Alternatively, the working end 36 of the catheter 34 can have a much enlarged dimension to form a bulbous shape which limits the amount of vein shrinkage around the working end. Different sized working ends and electrodes can be manufactured separately from the catheter shaft 44 for later assembly with the shaft 44 of the catheter so that a single catheter shaft 44 can be used with working ends having a variety of diameters. A working end having a specific size or shape could then be used with the catheter depending on the size and type of vein being treated. For example, certain larger veins may have a diameter of seven to fifteen millimeters (mm), while other veins may only have a diameter of three to five mm.

The catheter 34 includes a stranded, twisted center conductor 46 surrounded by a layer of insulation 48 (FIG. 7) which is preferably formed from TFE Teflon®. A silver coated copper braid 50 surrounds the insulated center conductor, and provides flexible and torqueable characteristics to the catheter shaft 44. A sheath 52 covers the copper braid 50, and is preferably made of an electrically resistive, biocompatible material with a low coefficient of friction such as Teflon®. The center conductor 46 is connected to a power source such as an RF generator, to provide RF energy to the electrodes 38 and 40. The power source can be controlled by a microprocessor in response to external commands or to data from a sensor located at the venous treatment site such as the temperature sensor 54 shown in FIG. 8. One electrode plate 38 can be in electrical connection with the center conductor 20 of the RF generator thus giving that electrode a "+" polarity. The other electrode plate 40 is connected to ground through the outer braid 50 thereby giving it a "−" polarity. The temperature sensor 54 is located between the electrodes 38 and 40. Other sensors may be used and may be mounted in other locations.

The catheter shaft 44 and electrodes 38 and 40 should be constructed from materials that would allow their visualization under fluoroscopy, X-ray, ultrasound or other imaging techniques. Preferably, shrinkage of the vein is detected by fluoroscopy or external ultrasound techniques. For example, a contrast medium can be injected into the vein to assess the condition of the vein and the relationship of the catheter to the treatment area of the vein by phlebography during the shrinkage process. The catheter 34 can also be configured to deliver x-ray contrast material. Alternatively, external ultrasound techniques such as B-scanning using distinct ultrasound signals from different angles to acquire a more multidimensional view of the vein shrinkage at the treatment site, which improves the detection of uneven shrinkage in the vein lumen than would otherwise be obtainable from a simple two-dimensional approach, can be used to assess vein shrinkage. Further, the multi-dimensional approach can assist in orienting the working end of the catheter in directionally applying RF energy to selected portions of the vein and venous valve. An angioscope can also be used to directly visualize the catheter, its position and orientation, and determine the degree of vein shrinkage.

As mentioned above, other techniques such as temperature monitoring, impedance monitoring, and ultrasonic pulse echoing, may be suitable for an automated system which shuts down or regulates the application of RF energy from the electrodes to the venous section when sufficient shrinkage of the vein is detected or to avoid charring or coagulation in the vein.

In one embodiment, the sensing element 54 comprises a temperature sensor such as a thermistor or a thermocouple. The temperature sensor can be included on the catheter near the electrodes on the working end to monitor the temperature surrounding the electrodes and the venous section being treated. A temperature sensor placed between the electrodes can provide a measure of vein tissue temperature. Monitoring the temperature of the vein tissue can provide a good indication of when shrinkage of the vein tissue is ready to begin. The collagen fibrils of vein tissue shrink at approximately 70° centigrade (C) or higher. Furthermore, monitoring a thermocouple temperature sensor placed on the electrode facing the vein wall can also provide an indication for when shrinkage occurs (i.e., 70° C. or higher) and when significant amounts of heat-induced coagulum form on the electrodes (i.e., 85° C.). Therefore maintaining the temperature between 70° to 85° degrees centigrade will produce a therapeutic shrinkage of the vein without forming significant amounts of coagulum. Application of RF energy from the electrodes is halted or reduced when the monitored temperature reaches or exceeds the specific temperature at which venous tissue begins to shrink. The signals from the temperature sensor can be input to a microprocessor which controls the magnitude of RF energy to the electrodes in accordance with the monitored temperature FIG. 11).

Instead of a temperature sensing element, another embodiment includes ultrasonic piezoelectric elements which emit pulsed ultrasound waves. The piezoelectric elements are operated in pulse-echo fashion to measure the distance to the vein wall from the catheter shaft. Again, the signals representative of the pulse-echo would be input to the microprocessor or to a monitor to allow for manual control, and the application of RF energy would be controlled accordingly.

Figure 9:
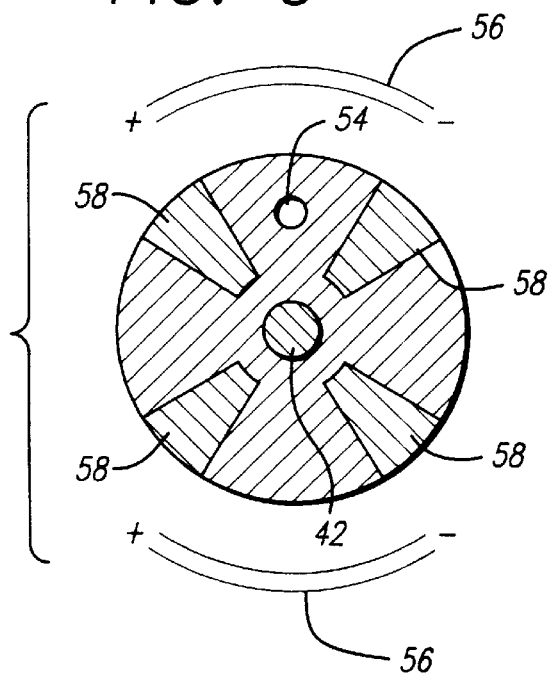
FIG. 9 is an end view of another embodiment of a catheter in accordance with aspects of the present invention.

FIG. 9 is an end view of an alternate embodiment of the catheter 34 having two pairs of discrete electrodes 58 at the working end One electrode from each pair is connected to a center conductor attached to the positive terminal from a bipolar RF generator. The other electrode from each pair is connected to the metal braid of the catheter which is attached to the negative terminal of the bipolar RF generator. The positive electrode of one pair is located adjacent the positive electrode of the other pair, as are the negative electrodes. This arrangement results in a directional application of RF energy from the catheter as RF current will flow primarily between electrodes of opposite polarity in the pairs of electrodes. Thus each electrode in FIG. 9 has two adjacent electrodes, one of like polarity and one of unlike polarity. The adjacent electrode of unlike polarity is of the same pair and the adjacent electrode like polarity is of the next adjacent pair. Current will therefore flow primarily along the flux lines 56 shown. A temperature sensor 54 is preferably located between the electrodes of unlike polarity. Where there is a central lumen 42 that can accommodate fluid delivery or a guide wire, the RF power leads are wound around the lumen liner made of HDPE or other polymers. The temperature sensor leads (not shown) run the length of the catheter to a thermocouple 54 located between the electrodes.

In FIG. 9, the electrodes are formed of metallic strips disposed on the outer surface of the distal tip or working end of the catheter. In another embodiment, the electrodes may be thicker and may be embedded in the distal tip. Additionally, more pairs of electrodes may be added depending on their size.

FIG. 10 presents yet another embodiment of the working end of a catheter where the electrodes comprise wires 60 (only one is shown) that are exposed for conducting RF energy to venous tissue. One wire would be connected to the RF generator to have a positive polarity while the other wire would be connected to the opposite or negative polarity. As shown in this embodiment, the center conductor 62 is wound around the guide wire lumen 42.

Another embodiment of the catheter including bowable electrodes disposed on the working end to cause localized heating of the surrounding venous tissue through the directional application of energy is shown in FIGS. 11 and 12. The catheter 64 includes four conductive elongate members 66 or arms (three can be seen) that can be bent or bowed outward. The elongate members 66 are surrounded by insulation, except for an exposed area that serves as the electrode 68 (shown in FIG. 12). Electrodes 68 that can be controllably moved outwardly from the catheter by these arms 66 will be referred to as bowable electrodes 66. The bowable electrodes 66 are formed along the circumference of the catheter 64, but are not fixed to the catheter. Bowing the electrodes outwardly also puts the electrodes in apposition with the venous tissue to be treated, and consistent contact of the electrode with the venous tissue can be maintained. The bowable electrodes preferably expand out to treat veins up to fifteen mm.

The bowable electrodes 66 are connected to a slidable tube 70 and a fixed tip 72 at the working end 74, where moving the tube 70 controls the diameter of the electrode deployment for proper treatment of vein lumen having different diameters. The inner stop tube 78 is connected to the slidable tube 70 and acts as a stop device as the slidable tube 70 and inner stop tube 78 are slid over the inner shaft 83 by making contact with the stop surface 80 that is fixed in position with the tip. The inner stop tube 78 thus interacts with the stop surface 80 to limit the amount of deployment of the bowable electrodes 66. A fluid cover 82, shown here in cutaway form as a bellows, prevents fluids from entering the space between the inner shaft 83 and the inner stop tube 78 and is discussed in greater detail below. A guide wire 98 is seen protruding out the working end 74.

As shown in FIG. 11, the bowable electrodes are connected to an RF generator 84. Also connected to the RF generator is a microprocessor 86. Each bowable electrode in this embodiment has a thermocouple temperature sensor 88 mounted at the electrode surface 68. Signals from the sensors 88 are coupled to the microprocessor 86 which compares them to a threshold temperature or temperatures to determine if RF energy to the electrodes should be interrupted or should be continued. The microprocessor 86 controls the RF generator 84 accordingly.

The catheter itself is fit through a suitably sized sheath for the procedure. For example, a seven French sheath, which has about a 2.3 mm diameter, may be used. The sheath is composed of a biocompatible material with a low coefficient of friction. The working end 74 of the catheter includes a tip 72 that is attached to one end of each electrode, and the other end of each electrode is connected to the sliding outer tube 70 formed along the exterior of the catheter shaft. The outer tube 70 extends down the length of the catheter to allow the physician to directly and mechanically control the effective electrode diameter during the application of RF energy. As the outer slidable tube 70 is moved towards and away from the working end in response to the control actuator 76, the electrodes 66 are urged radially outward and inward, respectively. The tip 72 essentially remains stationary while the outer tube is moved. Moving the outer tube 70 back toward the connecting end of the catheter pulls back and flattens the electrodes against the catheter before insertion or withdrawal from the vein. Moving the outer tube 70 forward toward the working end 74 of the catheter causes the electrodes to deflect and radially bow outward to an increased diameter. The contact area 68 of the electrodes is bowed outwardly as the opposite ends of the longitudinal electrode are moved closer together. The outer sleeve may be moved a preset distance to cause the electrodes to bow outwardly to a known diameter. Bowing the electrodes outwardly also places the electrodes in apposition with the venous tissue to be treated. By manipulating the slidable outer sleeve to adjust the effective diameter of the catheter defined by the radial bowing of the electrodes, contact between the electrodes and the venous tissue can be maintained during shrinkage.

The control actuator 76 is a switch, lever, threaded control knob, or any other suitable mechanism, preferably one that can provide fine control over the movement of the outer tube. By using the control actuator to move the tube, the effective diameter of the electrode can be controlled for treating vein lumina having different diameters, and for providing varying degrees of vein shrinkage. In another embodiment, a movable tip is connected to the actuator 76 by a control wire running through the catheter, so that the movable tip can be manually controlled by the actuator located at the connecting end of the catheter to cause the electrodes 66 to deploy or to contract.

The distal tip 72 is shown to have a nosecone shape, but can have other shapes that allow tracking of the catheter over the guide wire and through bends in the venous vascular system. The nosecone-shaped tip 72 can be fabricated from a polymer having a soft durometer, such as 70 Shore A. Alternatively, the tip can be constructed from a spring covered with a thin layer of polyethylene shrink tubing.

The bowable electrodes 66 can be bowed radially outward to treat specific sections or areas in the vein. As RF energy is applied to the bipolar electrodes, a discrete RF field is created around a portion of the catheter as defined by each active pair of the bowed electrodes. The RF field is directed toward specific venous tissue to be treated. The venous tissue becomes heated and begins to shrink. The extent of venous shrinkage is monitored by fluoroscopy, or any other suitable method. After sufficient shrinking the venous tissue has occurred, the application of RF energy from the electrodes 66 is ceased.

In order to prevent contamination from blood seeping back through the catheter, as shown in FIG. 12, a cover 82 is placed over the catheter shaft between the mounts for the bowable members and the stop devices 78 and 80. As the outer tube 70 slides over the catheter shaft, the cover 82 prevents blood from seeping back through the interface between these two catheter components. The cover is preferably manufactured from a flexible polymer such as a low density polyethylene. The cover 82 comprises accordion pleats taking the form of a bellows in one embodiment to allow the cover to expand and contract as the outer sleeve is moved to expand or retract the bowable electrodes 66, but may also take other forms such as a polymer tube. As the outer tube 70 is moved away from the tip 72, the electrodes are retracted towards the catheter by the bowable members, and the pleated folds of the cover 82 flatten out. As the outer tube 70 is moved toward the tip, the pleated folds would move closer together.

Turning now to FIGS. 12 and 13, the electrodes 66 may be fabricated from spring steel, stainless steel, or nitinol so that the electrodes 66 would be biased to return to a reduced diameter profile. The electrodes in one embodiment comprise flat strips to facilitate flexing of the catheter at the working end while being delivered through the bands of tenuous venous vasculature. The strips have relatively large flat surfaces for contacting the vein wall can be used. Such rectangular wires can have widths ranging from 0.005 to 0.05 inches, and preferably between 0.015 and 0.030 inches, to allow four or more electrodes around the catheter shaft. Rounded wires may also be used with a diameter preferably between about 0.005 to 0.015 inches (about 0.12 to 0.35 mm), but can be up to about 0.03 inches (about 0.7 mm).

The entire length of the bowable longitudinal electrode is conductive, and insulation 90 may be provided over the majority of the electrode surface in order to prevent any unintended heating effects. Only a modest portion of the conductive surface 68 is exposed to act as the electrode. The exposed surface can be placed closer to the tip 72 so that when the bowable electrodes are moved away from the catheter, the exposed conductive surface of the electrodes will be near the tip 72 which can be positioned adjacent the commissures and leaflets of the vein. The heating effect is greatest when the electrodes are close together since the electrical field density (power density) is greatest at this point. The ends of the electrodes are insulated from each other to prevent creating larger electrical field densities at the ends, especially as the effective diameter increases which would create even greater field disparities between the ends and the bowed midsection where the electrode gap is larger. The insulation 90 can be polyimide, paralyene, or another type of insulating film. Insulation 90 provided along the inner radius of the bowable electrodes away from the venous tissue further prevents heating the blood flowing in the vein and reduces the likelihood of coagulation. The remaining exposed area 68 of the electrode is preferably the area which contacts the venous tissue during apposition. The heating effect is then focused along that portion of the venous tissue and between the positive and negative electrodes. Where the arm 66 has a rectangular shape, then the exposed area which functionally acts as the electrode would then occupy only one face of that wire. The insulation 90 surrounding the electrode can further cover the peripheral edges of the exposed face of the electrode to further isolate the blood flow from unintended heating effects.

A sensor 88 such as a small thermocouple for measuring temperature is attached to the electrode 66. As shown in the cross-sectional view of FIG. 13 taken along lines 13—13 of FIG. 12, the temperature sensor 88 is soldered in place through a hole in the electrode so that the sensor is nearly or substantially flush with the exposed surface of the electrode. The sensor can accurately sense the temperature of the vein wall in apposition with the exposed electrode surface. The leads 92 to the sensor are situated on the opposite side of the electrode which is insulated.

As the electrodes are bowed outwardly toward the dilated diameter of the varicose vein, the gap between electrodes may increase which can weaken the RF field formed between the electrodes. Maintaining a constant gap or distance between the relevant electrodes of opposite polarity would allow a uniform RF field to be applied throughout the procedure as the vein diameter shrinks. Having a uniform RF field regardless of the diameter defined by the bowed out electrodes would also increase the predictability of the shrinkage. For the directional application of RF energy, one embodiment would have the bowable members containing the electrodes mounted on a rectangular or squarish mounting surface, as shown in FIG. 14. The electrodes 94 would lie roughly along the same plane, and would generally remain the same distance apart as the electrodes are moved outwardly by the parallel bowable members along the same plane. Preferably, a 1.0 to 1.5 mm gap is maintained between the electrodes forming the directional RF field.

FIG. 15 is an end schematic view of the working end of the bowable-electrode catheter 64 and the bowable electrodes 66 of FIGS. 11, 12 and 13. In the four-electrode configuration, a preferred embodiment is to have the two pairs of bowable electrodes 66 spaced apart along the circumference of the catheter to form discrete pairs of electrodes. Each electrode would have the opposite polarity from one of its adjacent electrodes and the same polarity as the other adjacent electrode. Electrodes of opposite polarity would form active electrode pairs to produce an RF field 96 between them. Thus, discrete RF fields 96 would be set up along the circumference of the catheter. In another embodiment, if the adjacent electrodes 66 all had opposite polarities to one another, but were moved closer together to form discrete electrode pairs, two opposite pairs of active electrodes would be formed along the circumference of the catheter. While an RF field would be formed along the entire circumference of the catheter, the RF field would be strongest between the closely adjacent electrodes in each pair of opposite electrodes. As a result, heating and shrinkage would be concentrated between the electrodes of opposite polarity with a small inter-electrode gap.

The working end of the catheter further includes a guide wire lumen 42 for accepting a guide wire 98. The tip of the guide wire 98 is preferably rounded. The guide wire lumen 42 is preferably insulated so as to prevent or minimize any coupling effect the electrodes 66 may have on the guide wire. The guide wire can be removed before the application of RF energy to the electrodes. The guide wire lumen can also allow for the delivery or perfusion of medicant and cooling solution to the treatment area during application of the RF energy.

Figure 16:
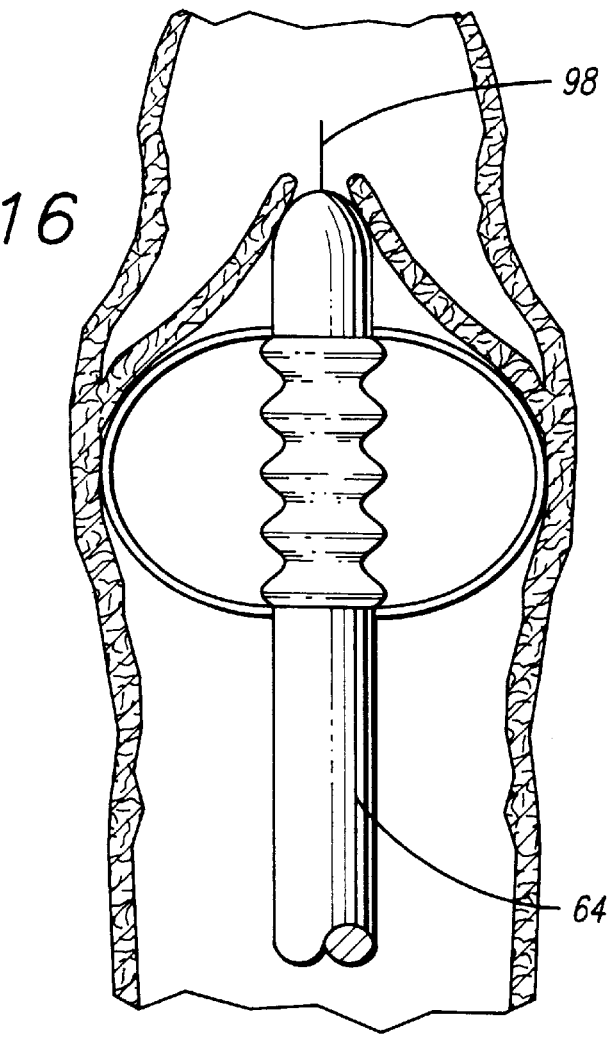
FIG. 16 is a representative side view of a valve of a venous section being treated by the embodiment of the catheter of FIG. 11 in accordance with aspects of the present invention.
Figure 17:
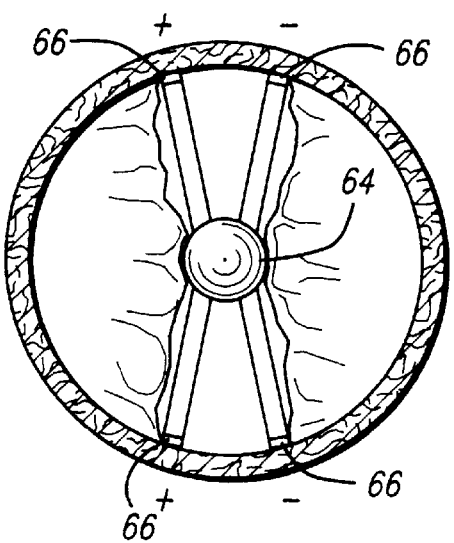
FIG. 17 is a front cross-sectional view of the commissures of the venous section being treated by the embodiment of the catheter of FIG. 11 in accordance with aspects of the present invention.
Figure 18:
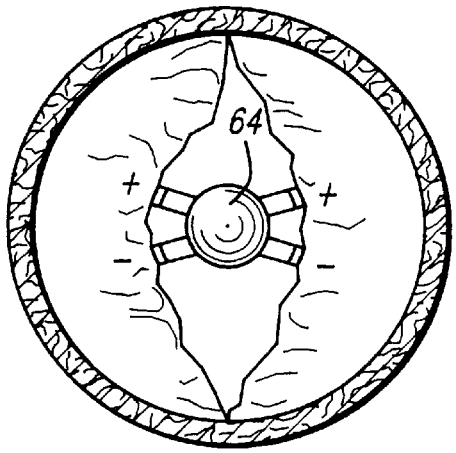
FIG. 18 is a front cross-sectional view of the leaflets of the valve of the venous section being treated by the embodiment of the catheter of FIG. 11 in accordance with aspects of the present invention.

FIG. 16 is a side view of the catheter of FIGS. 11, 12, and 13 being deployed from an antegrade approach to treat an incompetent valve. In FIG. 16, the leaflets are in contact with the bowable arms and RF energy may be applied just below them to the vein wall to reduce the diameter of the vein at the valve to restore valvular competency. FIGS. 17 and 18 present another approach where the commissures are first shrunk (FIG. 17) and then the catheter is used to impart RF energy to the leaflets, if needed (FIG. 18). As shown in the front view of FIG. 17, the bowable electrodes 66 are expanded outward to treat the commissures on opposite sides of the vein simultaneously. The application of RF energy heats and shrinks the venous tissue at the commissures in order to restore valve competency. The application of RF energy can be halted, and the catheter manipulated to treat the leaflets if necessary, by retracting the bowable electrodes toward the body of the catheter as shown in FIG. 18. The catheter may also be pushed forward so as to come into closer proximity to the valve. Such treatment allows valve leaflet shrinkage to restore the competency of the venous valve.

Another embodiment, shown in a side view in FIG. 19, is similar to that shown in FIGS. 11, 12, and 13 except that only one pair of electrodes 100 is included on the catheter 102. The electrodes 100 are a pair of longitudinal electrodes located on one side of the catheter which can be bowed outwardly. The electrodes 100 can have the same construction as the bowable electrodes described in connection with the embodiment illustrated in FIGS. 11, 12, and 13 for example. The operation of this embodiment is similar to that described previously, except that each of the commissures would be treated one at a time. As previously described and shown in FIG. 14, this catheter can be made in a manner to maintain a predetermined distance between the pairs of active electrodes despite outward bowing and diameter expansion.

Another embodiment, shown in plan view in FIG. 20 comprises a catheter 103 that uses an asymmetrical balloon 104 to deflect the electrodes 106 at the working end of the catheter to one side. The balloon 104 is located on the side of the catheter opposite to the electrode pair. When the balloon 104 is inflated, the opposite side of the working end accommodating the longitudinal electrodes 106 is moved into apposition with the venous tissue to be treated. After treating the dilated venous section, the balloon can be deflated, and the catheter removed from the vasculature. It should be noted that the other mechanisms for deflecting the working end of the catheter may be used. For example, a bendable actuation wire or strut may be used on one side of the catheter in order to perform a function similar to that of the asymmetrical balloon. Although not shown, the catheter is similar in internal construction to the previously discussed embodiments.

Figure 21:
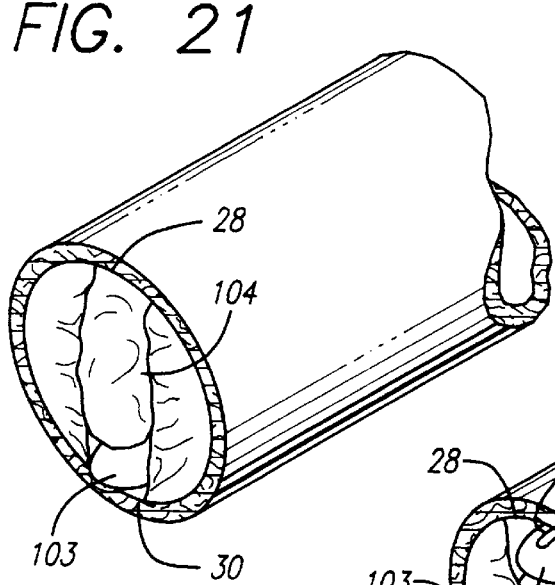
FIG. 21 is a representative view of a venous section having an incompetent valve which is being treated at one commissure by a catheter having an electrode pair (not shown) and an inflated balloon opposite the electrode pair to position the electrode pair in apposition with the commissure, in accordance with aspects of the present invention.
Figure 22:
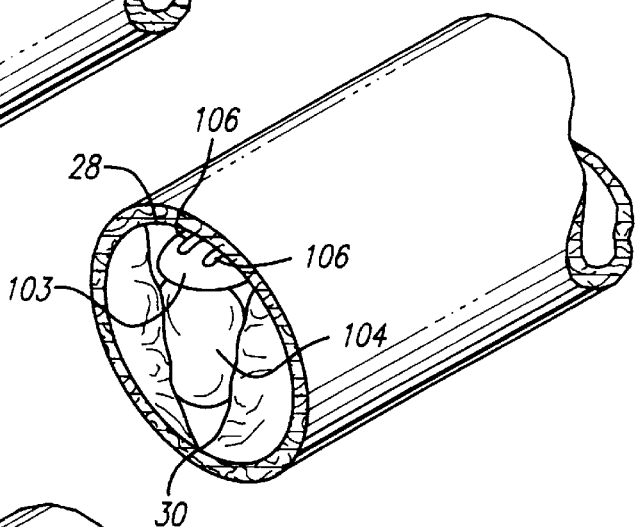
FIG. 22 is a view similar to FIG. 21 showing the electrode pair of the catheter of FIG. 21 positioned in apposition with the opposite commissure by the inflated balloon, in accordance with aspects of the present invention.
Figure 23:
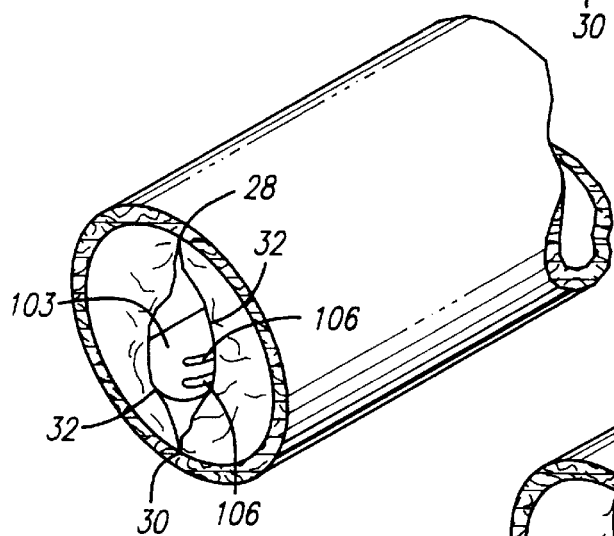
FIG. 23 is a cross-sectional view of treatment of a leaflet of the valve of FIGS. 21 and 22 in accordance with aspects of the present invention where the balloon has once again been inflated to position the electrode pair as desired.
Figure 24:
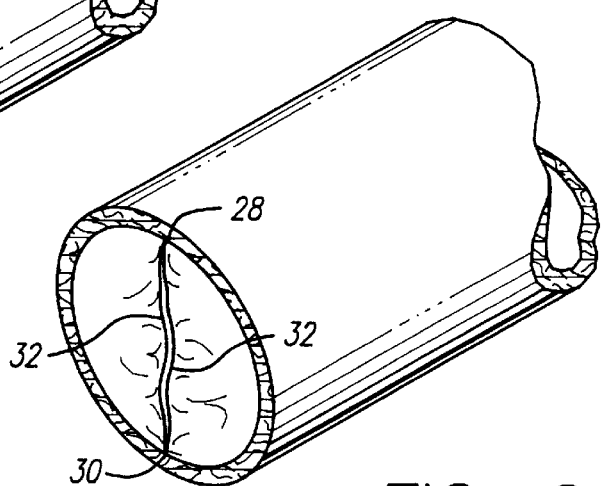
FIG. 24 is a view of a competent valve resulting from the activity shown in FIGS. 21 through 23.

FIGS. 21 through 24 present an example of an application of the directional energy application catheter 103, shown in FIG. 20. In FIG. 21, an incompetent valve taken along lines 2—2 of FIG. 1 is being treated at one commissure 30 by the catheter 103 of FIG. 20 having an electrode pair 106 (not shown) and an inflated balloon 104 opposite the electrode pair 106 to position the electrode pair in apposition with the commissure 30. In FIG. 21, the electrode pair 106 of the catheter 103 has been positioned by means of inflating the balloon 104 in apposition with the opposite commissure 28. Finally, in FIG. 23, the electrode catheter 103 has both electrodes 106 in apposition with one valve leaflet 32 to shrink the leaflet 32. Alternatively, apposition with only the commissure 28 or 30 may provide enough shrinkage of the vein so that contact with the leaflets 32 is not necessary.

The directional catheter shown in FIGS. 19 and 20 may also be used to reduce the size of or occlude an opening or ostium into a branch vein. Where such vein provides too great a flow into another vein, the ostium of the branch vein can be reduced in size to decrease the flow or occluded to terminate flow. In some cases, it is impractical to treat the branch vein itself; therefore, occluding its ostium may improve conditions. In such a case, a catheter such as that shown in FIGS. 19 and 20 may be used to heat the ostium or tissue adjacent the ostium to reduce its size. The electrodes would be positioned against the ostium wall by a positioning device, such as the balloon shown in FIG. 20 or the strut shown in FIG. 19, and energy applied to reduce the ostium size.

Figure 25:
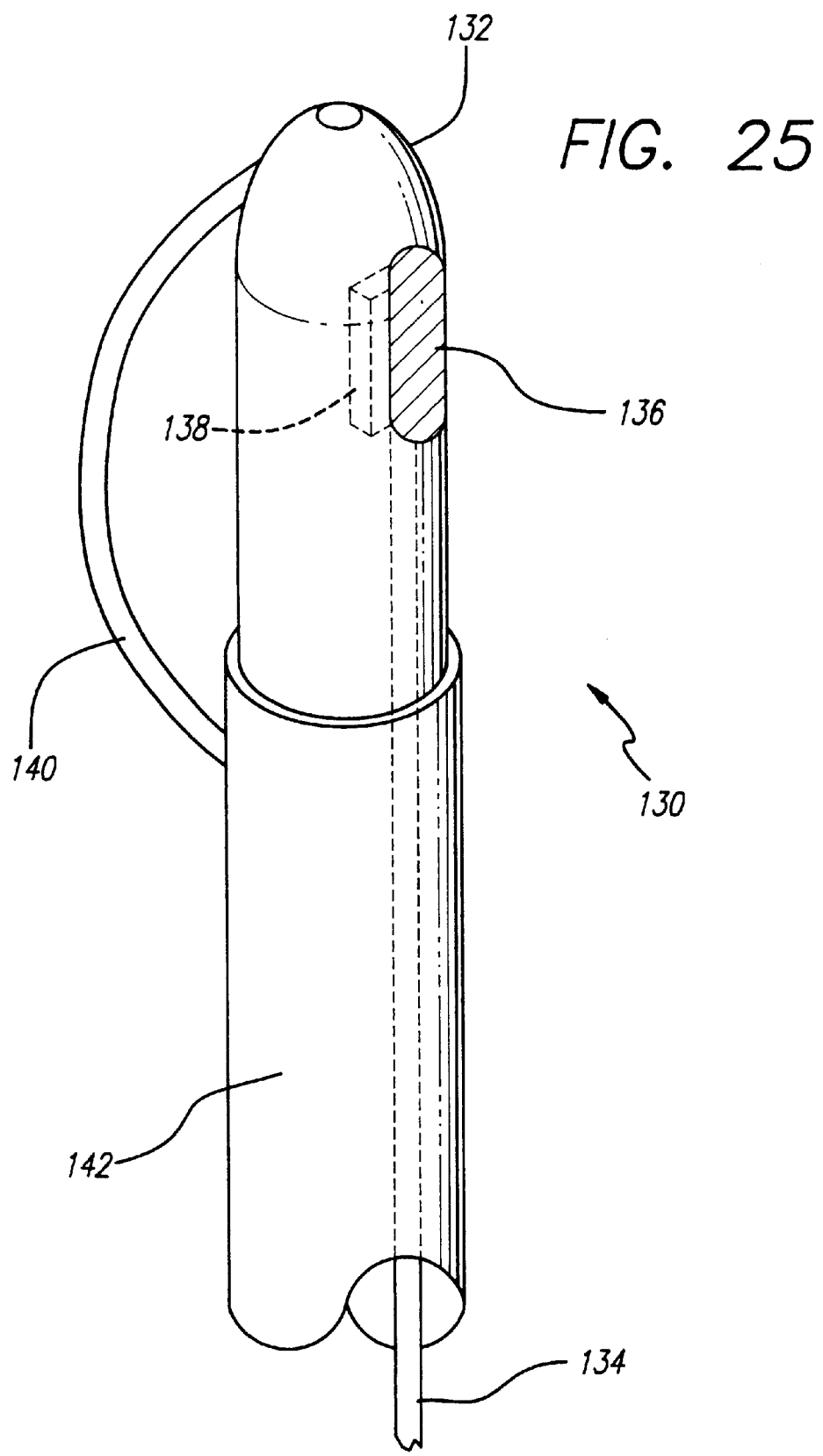
FIG. 25 is a view of an alternate embodiment of a directional catheter in which optical energy is directionally applied to the vein wall to cause shrinkage.

Referring now to FIG. 25, an alternate embodiment of a directional energy applying catheter is presented. In this embodiment, a catheter 130 having an optical fiber diffusing tip 132 is used to directionally apply energy to a selected vascular segment. As shown, an optical fiber 134 is disposed within the catheter 130 and is connected at its distal end to a light diffusing device 136, such as a sapphire crystal, to allow diffusion of optical energy, such as that produced by a LASER connected to the proximal end of the catheter. Additionally, the diffusing tip may have a reflector 138 to direct the optical energy toward the wall of the vein and away from the catheter lumen in which the optical fiber is located. Other light sources, such as a flash lamp may be used. A tip deflecting wire or strut 140 is shown in this embodiment to be deployed for placing the optical energy radiating tip 132 in apposition with the vein wall; however, other devices may be used for accurate placement of the energy source, such as a balloon shown in FIG. 20. The outer sleeve 142 of the catheter is slidable. Sliding it toward the distal tip results in the strut 140 expanding and sliding the sleeve in the proximal direction results in the strut 140 contracting.

As can be readily ascertained from the disclosure herein, the surgical procedure of the present invention is accomplished without the need for prolonged hospitalization or post-operative recovery. The restoration of venous function is possible without the need for continued lifestyle changes, such as frequent leg elevation, the wearing of elastic support stockings, or prolonged treatment of recurrent venous stasis ulcers. Moreover, the need for surgery of the arm and leg for transplantation of arm veins into the leg would not be necessary.

Early treatment of venous disease could prevent more serious complications such as ulceration, and valve damage caused by thrombophlebitis or thromboembolism. The cost of treatment and complications due to venous disease would be significantly reduced. There would be no need for extensive hospitalization for this procedure, and the need for subsequent treatment and hospitalization would also be reduced from what is currently needed. Furthermore, the minimally invasive nature of the disclosed methods would allow the medical practitioner to repair or treat several vein sections in a single procedure in a relatively short period of time.

It is to be understood that the type and dimensions of the catheter and electrodes may be selected according to the size of the vein to be treated. Although the present invention has been described as treating venous insufficiency of the lower limb such as varicose veins in the leg, the present invention can be used to intraluminally treat venous insufficiency in other areas of the body. For example, hemorrhoids may be characterized as outpocketed varicose veins in the anal region. Traditional treatments include invasive surgery, elastic ring ligation, and the application of topical ointments. Shrinking the dilated veins using RF energy can be accomplished in accordance with the present invention. Specifically, the catheter and electrode combination is introduced into the venous system, into the external iliac vein, the internal iliac vein, then either the hemorrhoidal or the pudendal vein. The catheter then delivers the electrode to the site of the dilated hemorrhoidal vein by this transvenous approach. Fluoroscopic techniques or any other suitable technique such as pulse-echo ultrasound, as previously discussed, can be used to properly position the electrode at the venous treatment site. The treatment site is preferably selected to be at least two centimeters above the dentate line to minimize pain. The electrode applies RF energy at a suitable frequency to minimized coagulation for a sufficient amount of time to shrink, stiffen, and fixate the vein, yet maintain venous function or valvular competency. This intraluminal approach avoids the risks and morbidity associated with more invasive surgical techniques such as hemorrhoidectomy, while significantly reducing reflux of blood in the area without necrosing or removing the venous tissue.

Another area of venous insufficiency relates to erectile impotency of the penis. A significant number of all physically-induced cases of impotence result from excessive drainage of blood from the penile venous system. Venous-drainage-impotence can be treated using the present invention. Catheters having a sufficiently small diameter can be used to deliver the electrodes through the dorsal vein of the penile venous system to shrink this venous outflow path.. Fluoroscopic or ultrasound techniques can be used to properly position the electrode within the incompetent vein. RF energy or other radiant energy is applied from the electrodes at a suitable frequency to shrink the surrounding venous tissue in order to reduce the excessive amount of drainage from the penis while maintaining venous function or valvular competency. The amount of shrinkage of the vein can be limited by the diameter of the catheter itself, or the catheter or electrodes themselves can be expanded to the appropriate size. Ligation of these veins should be avoided so as to allow for the proper drainage of blood from an engorged penis which is necessary for proper penile function.

Another area of venous insufficiency suitable for treatment in accordance with the present invention involves esophageal varices. Varicose veins called esophageal varices can form in the venous system along the submucosa of the lower esophagus, and bleeding can occur from the swollen veins. Properly sized catheters can be used in accordance with the present invention to deliver the electrodes to the site of venous insufficiency along the esophageal varices. Endovascular access for the catheter is preferably provided through the superior mesenteric vein or portal vein to shrink the portal vein branches leading to the lower esophagus. Proper positioning of the electrode within the vein can be confirmed using fluoroscopic or ultrasound techniques. The electrodes apply RF energy or other radiant energy at a suitable frequency to shrink the vein and reduce the swelling and transmission of high portal venous pressure to the veins surrounding the esophagus.

While several particular forms of the invention have been illustrated and described, it will be apparent that various modifications can be made without departing from the spirit and scope of the invention. Accordingly, it is not intended that the invention be limited, except as by the appended claims.

What is claimed:

1. A method of applying energy to cause shrinkage of a vein lumen, the method comprising the steps of:
    introducing a catheter having a working end with an energy application apparatus located at the working end, to a treatment site in the vein lumen;
    positioning the energy application apparatus adjacent the treatment site in the vein lumen;
    directionally emitting energy from the energy application apparatus to selectively heat the treatment site and cause shrinkage of a selected area of the vein lumen at the treatment site; and
    terminating the emission of energy from the energy application apparatus after causing sufficient shrinkage of the vein lumen to restore valvular competency while maintaining venous patency.

2. The method of claim 1 further comprising the step of determining the occurrence of shrinkage of the vein using fluoroscopy.

3. The method of claim 1 wherein the step of positioning the energy application apparatus at the treatment site further includes the step of placing the energy application apparatus at a commissure of a venous valve of the treatment site.

4. The method of claim 3 further including the step of positioning the energy application apparatus adjacent leaflets of the valve, after the step of placing the energy application apparatus at the commissure of the venous valve of the treatment site.

5. The method of claim 1 wherein the step of directionally emitting energy further includes the step of producing at least two discrete RF fields at the working end of the catheter by the energy application apparatus to directionally heat at least two separated venous sites at the treatment site simultaneously.

6. The method of claim 1 wherein the step of directionally emitting energy further includes the step of producing a discrete RF field along a portion of the circumference of the catheter by the energy application apparatus to directionally heat the venous tissue.

7. The method of claim 6 wherein the step of producing the discrete RF field includes the step of positioning the catheter to treat the commissure of the venous valve, and then the leaflets of the venous valve.

8. The method of claim 1 wherein the step for directionally emitting energy comprises the step of passing radio frequency energy between a positive polarity electrode and a negative polarity electrode to create an RF field along a portion of the catheter.

9. The method of claim 1 wherein the step of directionally emitting energy comprises the step of directionally emitting optical energy to selectively heat the treatment site.

10. The method of claim 9 wherein the step of directionally emitting optical energy comprises the further step of reflecting optical energy at the working end of the catheter to create a directional emission of energy for selectively heating the treatment site.

11. The method of claim 1 further comprising the step of palpating the vein into apposition with the energy application apparatus of the catheter in the vein lumen.

12. The method of claim 1 further comprising the steps of locating the working end of the catheter in apposition with the vein wall adjacent a selected commissure and directionally emitting energy to the vein wall to shrink the commissure.

13. The method of claim 1 further comprising the step of expanding the energy application apparatus radially outward from the working end and into apposition with the vein wall and directionally emitting energy to the vein wall to cause preferential shrinkage of venous tissue at the wall.

14. The method of claim 13 wherein the step of expanding comprises the step of expanding at least two pairs of electrodes from the working end into apposition with the vein wall, wherein each pair of electrodes comprises a discrete pair of opposite polarity electrodes and the electrodes within each discrete pair are arranged such that an electrode in one discrete pair is adjacent a like polarity electrode of the adjacent pair.

15. The method of claim 14 wherein the step of expanding comprises the step of expanding an even number of electrodes into apposition with the vein wall, wherein said even number comprises at least four, and wherein said even number of electrodes are disposed in a plurality of discrete pairs of opposite polarity electrodes, said electrodes in each discrete pair being arranged such that an electrode in one discrete pair is adjacent a like polarity electrode of an adjacent pair.

16. The method of claim 1 further comprising the step of determining the occurrence of shrinkage of the vein using ultrasonographic imaging.

17. The method of claim 1 wherein the step of positioning the energy application apparatus at the treatment site further includes the step of placing the energy application apparatus at an ostium and applying energy to reduce the size of the ostium.

18. A method of applying energy to cause the shrinkage of a vein to restore valvular competency, the method comprising the steps of:
    introducing a catheter having a working end and at least two electrodes located at the working end, to a treatment site in the vein;
    positioning the at least two electrodes adjacent venous tissue at the treatment site in the vein;
    applying high frequency energy from the electrodes to heat the treatment site and cause a reduction in the size of the vein; and
    terminating the application of energy from the electrodes after the size of the vein is reduced so that valvular competency is restored and patency of the vein is maintained.

19. The method of claim 18 further comprising the step of determining the occurrence of shrinkage of the vein using fluoroscopy.

20. The method of claim 18 further comprising the step of determining the occurrence of shrinkage of the vein using ultrasonographic imaging.

21. The method of claim 18 wherein the step of applying high frequency energy further includes the step of applying radio frequency energy between the at least two electrodes.

22. The method of claim 18 wherein the step of emitting high frequency energy further includes the step of producing a discrete RF field along a portion of the circumference of the catheter to directionally heat the venous tissue.

23. The method of claim 22 wherein the step of producing the discrete RF field includes the step of positioning the catheter to treat the commissures of the venous valve, and then the leaflets of the venous valve.

24. The method of claim 18 wherein the step of positioning the at least two electrodes at the treatment site further includes the step of placing the at least two electrodes at a commissure of the venous valve of the treatment site.

25. The method of claim 24 further including the step of placing the electrodes adjacent the leaflets of the valve after the step of placing the electrodes at the commissure of the venous valve of the treatment site.

26. The method of claim 18 wherein the step of emitting energy further includes the step of producing at least two discrete RF fields along the circumference of the catheter to directionally heat the venous tissue so that both commissures of the venous valve at the treatment site can be treated simultaneously.

27. The method of claim 18 further comprising the step of extending the electrodes away from the catheter to increase the effective diameter of the catheter.

28. The method of claim 27 further comprising the step of deploying an expandable member coupled to the working end to selectively position the two electrodes against selected venous tissue.

29. The method of claim 28 wherein the step of extending comprises the step of expanding at least two pairs of electrodes from the working end into apposition with the vein wall, wherein each pair of electrodes comprises a discrete pair of opposite polarity electrodes and the electrodes within each discrete pair are arranged such that an electrode in one discrete pair is adjacent a like polarity electrode of the adjacent pair.

30. The method of claim 29 wherein the step of expanding comprises the step of expanding an even number of electrodes into apposition with the vein wall, wherein said even number comprises at least four, and wherein said even number of electrodes are disposed in a plurality of discrete pairs of opposite polarity electrodes, said electrodes in each discrete pair being arranged such that an electrode in one discrete pair is adjacent a like polarity electrode of an adjacent pair.

31. The method of claim 18 further comprising the step of palpating the vein into apposition with the electrodes of the catheter in the vein lumen.

32. The method of claim 18 further comprising the steps of locating the working end of the catheter in apposition with the vein wall adjacent a selected commissure and directionally emitting energy to the vein wall to shrink the commissure.

33. The method of claim 18 wherein the step of positioning the energy application apparatus at the treatment site further includes the step of placing the energy application apparatus at an ostium and applying energy to reduce the size of the ostium.

* * * * *